United States Patent [19]
Bessling et al.

[11] Patent Number: 6,123,812
[45] Date of Patent: Sep. 26, 2000

[54] PROCESS FOR DISTILLING ETHYLENE OXIDE

[75] Inventors: Bernd Bessling, Grünstadt; Sebastian Zeck, Freinsheim; Jürgen Plückhan, Frankenthal; Thomas Mayer, Wachenheim; Ulrich Löffler, Dannstadt-Schauernheim; Günter Spiegel, Worms; Rubens Ballenweg, Weinheim; Gerhard Brudi, Ludwigshafen; Klaus Gieselberg, Laumersheim; Lutz Hilprecht, Ludwigshafen; Winfried Terjung, Oberhausen; Heinz Auer, Neulussheim; Axel Werner Polt, Deidesheim; Stephan Scholl, Bad Dürkheim, all of Germany

[73] Assignee: BASF Aktiengesellschaft, Ludwigshafen, Germany

[21] Appl. No.: 09/068,549

[22] PCT Filed: Nov. 5, 1996

[86] PCT No.: PCT/EP96/04818

§ 371 Date: May 18, 1998

§ 102(e) Date: May 18, 1998

[87] PCT Pub. No.: WO97/19069

PCT Pub. Date: May 29, 1997

[30] Foreign Application Priority Data

Nov. 17, 1995 [DE] Germany .............. 195 42 829

[51] Int. Cl.$^7$ .............. B01D 3/34; B01D 3/42; C07D 301/32
[52] U.S. Cl. .............. 203/2; 203/6; 203/14; 203/91; 203/99; 203/DIG. 19; 549/541
[58] Field of Search .............. 203/99, DIG. 19, 203/91, 6, 2, 14, 86; 202/158; 549/541

[56] References Cited

U.S. PATENT DOCUMENTS

| | | | |
|---|---|---|---|
| 4,134,797 | 1/1979 | Ozero | 203/99 |
| 5,244,604 | 9/1993 | Miller et al. | 261/97 |

FOREIGN PATENT DOCUMENTS

| | | |
|---|---|---|
| 28 50 254 | 5/1980 | Germany . |
| 29 46 080 | 5/1981 | Germany . |

OTHER PUBLICATIONS

B. Bessling, U. Loeffler and A. Polt, "Ethylenoxid–Reindestillation: Durch eine ganzheitliche Betrachtungsweize zu einem integrierten Verfahrens –und Sicherheitskonzept" siehe das ganze Dokument; Dec. 12, 1995, pp. 1614–1618.

Ullmann's Encyclopedia of Industrial Chemistry, "Ethylene Oxide" Bd., 1987, 5$^{th}$ Ed. vol. #10, pp. 117–135.

Ullmann's Encyclopedia of Industrial Chemistry, "Distillation and Rectification", vol. B3, 5$^{th}$ Ed. pp. 4–82 to 4–94.

Reinhard Billet, "Packed Towers in Processing and Environmental Technology", Verlag Chemie, Weinheim, 1995, pp. 25 to 27.

Grundlagen, Auslegung, Apparate, Klaus Sattler: "Thermische Trennverfahren", Verlag Chemie, Weinheim 1988, pp. 25 to 27.

*Primary Examiner*—Virginia Manoharan
*Attorney, Agent, or Firm*—Oblon, Spivak, McClelland, Maier & Neustadt, P.C.

[57] ABSTRACT

A process for distilling ethylene oxide out of a mixture including ethylene oxide in a column at an absolute pressure of from 2 to 10 bar and a temperature of 20 to 180° C. by withdrawing pure ethylene oxide in the liquid or gaseous state overhead or via a sidestream in the rectifying section of the column includes effecting the distillation in a column having on its inside a plurality of successive zones of structured sheet-metal packing or dumped beds of packing elements, these zones being assigned one or more extinguishing systems on the outside of the column.

11 Claims, No Drawings

PROCESS FOR DISTILLING ETHYLENE OXIDE

DESCRIPTION

The present invention relates to a novel process for distilling ethylene oxide out of a mixture comprising ethylene oxide in a column by withdrawing pure ethylene oxide overhead or via a sidestream in the rectifying section of the column.

Ethylene oxide can be prepared by oxidation of ethylene with oxygen. The oxidation generally takes place in a fixed-bed reactor at from 230 to 270° C. (Ullmann's Encyclopedia of Industrial Chemistry, 5th Ed., Vol. A 10, pages 117 to 135).

The ethylene oxide production reactor effluent, which comprises ethylene oxide, ethylene, carbon dioxide, acetaldehyde and also low boilers, such as methane, is treated with water to remove ethylene oxide. Ethylene oxide can be isolated in pure form from the resulting mixture of ethylene oxide and water by distilling the mixture after removal of the low boilers.

Ethylene oxide is a significant intermediate in the chemical industry because of its high reactivity. It is used for example for the synthesis of ethylene glycol, ethylene glycol ethers, oligo- or polyethylene glycols or ethanolamines.

On the other hand, the high reactivity of ethylene oxide is a problem when it comes to distilling the ethylene oxide, since it can decompose explosively under distillation conditions when subjected to the action of a source of ignition. In addition, as mentioned, it can form glycols with the water likewise present.

It is an object of the present invention to provide a novel process for distilling ethylene oxide out of a mixture comprising ethylene oxide wherein the decomposition reaction of ethylene oxide, in particular in its initial stages, is completely suppressed or terminated.

We have found that this object is achieved by a process for distilling ethylene oxide out of a mixture comprising ethylene oxide in a column at an absolute pressure of from 2 to 10 bar and a temperature of from 20 to 180° C. by withdrawing pure ethylene oxide in the liquid or gaseous state overhead or via a sidestream in the rectifying section of the column, which comprises feeding the mixture through a plurality of successive zones of structured sheet-metal packing or dumped beds of packing elements, at least one of which zones is connected to an extinguishing system via which a liquid solvent which is miscible with ethylene oxide is fed into the zone(s) from outside the column as soon as the pressure limit in the column is exceeded.

Preferably the mixture to be distilled comes from the synthesis of ethylene oxide and includes water as well as ethylene oxide. Examples of further possible ingredients in this case are ethylene glycol, oligo(ethylene glycol)s, aldehydes, such as formaldehyde or acetaldehyde, and methane.

However, it is also possible to apply the process of this invention to the distillation of mixtures which, besides ethylene oxide, include for example methanol, glycols, mono-, di- or triethanolamine or mono- or di($C_1$–$C_4$ alkyl) ethanolamines.

Preferably the mixture to be distilled comprises, in each case based on its weight, from 10 to 90% by weight, preferably 30 to 70% by weight, of ethylene oxide and from 90 to 10% weight, preferably from 70 to 30% by weight, of water. The mixture may further comprise, in each case based on its weight, from 0 to 10% by weight, preferably 0 to 5% by weight, of ethylene glycol and from 0 to 10% by weight, preferably 0 to 5% by weight, of acetaldehyde. It will be appreciated that the sum of the ingredients of the mixture is 100% by weight in each case.

According to the invention, the novel process is carried out in a column, preferably having a rectifying section. Suitable columns include customary, known distillation columns as described for example in Ullmann's Encyclopedia of Industrial Chemistry, 5th ed., vol. B3, pages 4–82 to 4–94, or in Klaus Sattler, Thermische Trennverfahren: Grundlagen, Auslegung, Apparate, Verlag Chemie, 1988, pages 25 to 27.

The columns have on their inside a plurality of successive zones of structured sheet-metal packing or dumped beds of packing elements. It is a central consideration that the particular way in which the mixture to be distilled is fed through these zones makes it possible to achieve excellent distillative separation and also to counteract the decomposition of ethylene oxide. It can be of advantage in this connection to provide, on the inside of the column, additional zones of structured sheet-metal packing or dumped packing which act as decomposition barriers only.

Suitable packing elements include for example the well known Raschig rings, Pall rings or Bialecki rings in metal or ceramic. Suitable structured sheet-metal packings are likewise known and commercially available for example under the designations Gempak® (Glitsch, Inc. Dallas, Tex., U.S.A.), Mellapak® (Gebr. Sulzer, Winterthur, Switzerland) or Relapak®. They are described for example in Ullmann's Encyclopedia (loc. cit.) or in Reinhard Billet, Packed Towers in Processing and Environmetal Technology, Verlag Chemie, Weinheim, 1995, pages 25 to 27.

As well as these zones, the distillation column includes customary collector and distributor systems.

The specific surface area of a structured sheet-metal packing zone ranges in general from 100 to 1000 $m^2$, preferably from 125 to 750 $m^2$, based on one $m^3$ of the sheet-metal packing zone.

The specific surface area of a dumped-packing zone ranges in general from 100 to 1000 $m^2$, based on one $m^3$ of the dumped-packing zone.

Preferably the distillation is carried out in a column having a plurality of zones of structured sheet-metal packing.

With particular advantage the novel process is carried out in a column having from 2 to 20, preferably 3 to 15, in particular 4 to 8 and most preferably from 4 to 6 of these structured sheetmetal packing zones.

The height of the individual packing zones ranges from 1 to 15 m, preferably from 3 to 8 m.

The sheet-metal packing or dumped-packing zones are connected to one or more extinguishing systems disposed outside the column.

The extinguishing system, in general an extinguishant-filled container which may additionally include [lacuna] small amount of an inert gas, for example nitrogen, is connected to the column by means of pipework and conventional measuring and control means. In effect the extinguishant can be passed into the column by means of pumps, for example after the opening of valves. In a preferred embodiment of the process of this invention, the extinguishing systems are disposed above the abovementioned zones. In this way the hydrostatic pressure of the extinguishant is utilized in the process of extinguishment.

The customary collector and distributor systems present in the column can be utilized with advantage to ensure the optimum distribution of the extinguishant in the column.

Suitable extinguishants are liquids which are miscible with ethylene oxide. An aqueous medium is preferred. Water is particularly preferred. The water extinguishant, for example cooling water or river water, may additionally comprise assistants, for example an antifreeze.

An explosive decomposition of gaseous ethylene oxide is associated with an increase in the pressure up to ten times the initial pressure. If liquid ethylene oxide decomposes, an even higher pressure can be reached, owing to the decomposition gases formed. Extinguishment is triggered when an adjustable pressure limit is exceeded. This limit is generally within the range from 0.01 to 4 bar, preferably from 0.1 to 2 bar, particularly preferably from 0.2 to 1 bar, in particular about 0.5 bar, above the operating pressure in the column. The extinguishant enters the packing zones after a period of from about 5 to 60 seconds, preferably about 15 seconds.

In the event of a downward moving decomposition, the decomposition front travels faster than the extinguishment front. In this case decomposition is stopped only in the next packing zone, since this region has already been flushed with extinguishant and the conditions prevailing there therefore do not permit any further decomposition of ethylene oxide. In the event of an upward moving decomposition, the decomposition front and the extinguishment front travel toward each other and meet, which results in extinguishment.

Preferably, in extinguishment, sufficient extinguishant, preferably water, is passed into the column that the weight ratio of ethylene oxide:extinguishant in the region to be extinguished between two packing zones is below 80:20, preferably below 70:30, at the time of extinguishment.

Preference is given to a procedure where each sheet-metal packing or dumped-packing zone is connected to a separate extinguishing system.

Advantageously the extinguishant container of the uppermost extinguishing system is designed to be larger than the container of the remaining extinguishing systems. When this container is designed to be from about 1.5 to 2 times larger, this ensures that further extinguishant can flow into the entire column, additionally intensifying the process of extinguishment.

In the process of this invention, which is carried out in a continuous manner, the ethylene oxide mixture to be distilled is fed into the column at a point from about 30 to 80%, preferably about 50%, up the length of the column. The reflux ratio ranges from 1.5:1 to 6:1, preferably from 2.5:1 to 3.5:1. The distillation is effected at an absolute pressure of 2 to 10 bar, preferably from 2.5 to 4 bar, and at a temperature of from 10 to 180° C., preferably from 30 to 150° C.

Pure ethylene oxide is withdrawn overhead or via a sidestream in the rectifying section of the column.

Preference is given to a procedure where pure ethylene oxide is withdrawn in the gaseous state overhead or in the gaseous or liquid state via a sidestream.

When ethylene oxide is withdrawn via a sidestream in the rectifying section of the column, low boilers, for example formaldehyde, can advantageously be withdrawn as overhead product.

In the distillation of a mixture comprising ethylene oxide and water, water is generally withdrawn as bottom product.

In the distillation of a mixture comprising ethylene oxide, water and acetaldehyde, it is preferable to withdraw pure ethylene oxide overhead, a mixture comprising acetaldehyde, ethylene oxide and water via a sidestream in the stripping section of the column, and water as bottom product.

In the distillation of a mixture comprising ethylene oxide, water, formaldehyde and acetaldehyde, it is preferable to withdraw a mixture of a formaldehyde and ethylene oxide overhead, pure ethylene oxide via a side stream in the rectifying section of the column, a mixture comprising acetaldehyde, ethylene oxide and water via a side stream in the stripping section of the column, and water as bottom product.

The amount of heat required for the distillation can be supplied in various ways. For example, it can be supplied at the base of the column, in the stripping section of the column or by heating the feed in the distillation of a mixture comprising ethylene oxide and water. In the distillation of a mixture comprising ethylene oxide and water it is of particular advantage to effect the heat supply in the stripping section of the column or by heating the feed, since the aqueous system inherently provides an extinguishant which counteracts the decomposition of ethylene oxide.

A particularly preferred procedure comprises effecting the distillation in a column which is jacketed and flushing the space between column and jacket with an inert gas, for example carbon dioxide or nitrogen, preferably nitrogen. These measures provide additional protection against external sources of ignition which can initiate the explosive decomposition of ethylene oxide.

The novel process provides an advantageous way of continuously distilling ethylene oxide out of a mixture comprising ethylene oxide while ensuring that, if spontaneous decomposition of ethylene oxide does occur, it can be immediately brought under control without explosion-based destruction of the distillation plant. The purity of the ethylene oxide obtained in the process of this invention is very high. For example, the ethylene oxide obtained in the distillation of an aqueous reaction mixture from the synthesis of ethylene oxide has an acetaldehyde content of not more than 30 ppm and a water content of not more than 60 ppm.

We claim:

1. A process for distilling ethylene oxide out of a mixture comprising ethylene oxide in a column at an absolute pressure of from 2 to 10 bar and a temperature of from 20 to 180° C. by withdrawing pure ethylene oxide in the liquid or gaseous state overhead or via a sidestream in a rectifying section of the column, which comprises feeding the mixture through a plurality of successive zones of structured sheet-metal packing or dumped beds of packing elements, which zones are located inside the column and at least one of which is connected to an extinguishing system containing an extinguishant, and feeding a liquid solvent which is miscible with ethylene oxide from the extinguishing system into the zone(s) from outside the column as soon as the pressure limit in the column is exceeded, wherein said plurality of successive zones acts at least as decomposition barriers.

2. A process as claimed in claim 1, wherein the mixture to be distilled comprises ethylene oxide and water.

3. A process as claimed in claim 2, wherein the mixture to be distilled comprises, based on its weight, from 10 to 90% by weight of ethylene oxide and from 90 to 10% by weight of water.

4. A process as claimed in claim 1, wherein the specific surface area of a zone of structured sheet-metal packing is from 100 to 1000 m$^2$ per m$^3$ of the metal-packing zone.

5. A process as claimed in claim 1, wherein the specific surface area of a zone of dumped beds of packing elements is from 100 to 1000 m$^2$ per m$^3$ of the dumped-packing zone.

6. A process as claimed in claim 1, wherein the distillation is effected in a column having a plurality of zones of structured sheet-metal packing.

7. A process as claimed in claim 1, wherein the distillation is carried out in a column having from 2 to 20 zones of structured sheet-metal packing.

8. A process as claimed in claim 1, wherein each metal-packing or dumped-packing zone is connected to a separate extinguishing system.

9. A process as claimed in claim 1, wherein the extinguishant used is an aqueous medium.

10. A process as claimed in claim 1, wherein the solvent is passed into the zone(s) as soon as the pressure in the column exceeds the operating pressure by from 0.01 to 4 bar.

11. The process as claimed in claim 1, wherein the pure ethylene oxide has an acetaldehyde content of not more than 30 ppm and a water content of not more than 60 ppm.

* * * * *